United States Patent [19]
Keyes

[11] 4,008,126
[45] Feb. 15, 1977

[54] IMMOBILIZATION OF PROTEINS BY IN-SITU POLYMERIZATION
[75] Inventor: Melvin H. Keyes, Sylvania, Ohio
[73] Assignee: Owens-Illinois, Inc., Toledo, Ohio
[22] Filed: Mar. 15, 1976
[21] Appl. No.: 666,819
[52] U.S. Cl. .................................. 195/63; 195/68; 195/DIG. 11; 260/112 R
[51] Int. Cl.$^2$ .......................................... C07G 7/02
[58] Field of Search ............... 195/63, 68, DIG. 11; 260/112 R

[56] References Cited
OTHER PUBLICATIONS

Fishbein et al., Archieves of Biochemistry and Biophysics, vol. 144, pp. 700–714 (1971).

Fishbein et al., Archieves of Biochemistry and Biophysics, vol. 151, pp. 370–377 (1972).

*Primary Examiner*—Lionel M. Shapiro
*Attorney, Agent, or Firm*—Howard G. Bruss, Jr.; E. J. Holler; Richard B. Dence

[57] ABSTRACT

Disclosed is a method for chemically immobilizing proteins, particularly enzymes, containing in their molecular structure specified proportions cystine and cysteine groups on a support to form a biologically active composite having prolonged service life by the in-situ polymerization of the protein.

18 Claims, No Drawings

IMMOBILIZATION OF PROTEINS BY IN-SITU POLYMERIZATION

Enzymes are biologically active proteins which catalyze specific reactions. Enzymes have been used for a wide variety of industrial and research applications, particularly in fermentation, pharmaceuticals, medical research, and food processing. They are highly specific in their biological activity and generally do not generate significant quantities of undesirable by-products.

Recently attempts have been made to chemically or physically immobilize enzymes on various supports in the interest of efficient recovery and reuse. In the past, enzymes have been immobilized by attachment to inorganic supporting matrices by covalent coupling, adsorption, and ionic bonding. Covalent coupling of enzymes to water insoluble supports has been intensively investigated. Most of the supports have been organic polymers although recent reports have appeared where coupling agents have been used to attach enzymes to ceramic materials.

Adsorption of enzymes to water insoluble supports, whether organic or inorganic, has been the simplest insolubilization technique. It has been attractive because it requires merely exposing the enzyme in solution to the support material. The ease of adsorption, however, is offset by the corresponding ease of desorption. U.S. Pat. Nos. 3,556,945 and 3,850,751 disclose techniques for adsorption of enzymes to porous inorganic supports.

Another technique to immobilize enzymes is to adsorb them onto inert, i.e. non-reactive, supports and crosslink the enzyme with bifunctional crosslinking reagents. Examples of such techniques are given in U.S. Pat. No. 3,705,084 and the article entitled "Papain-Collodion Membranes. I. Preparation and Properties" by R. Goldman, O. Kedem, I. Silman, S. Caplan, and E. Katchalski appearing in the February 1968 issue of Biochemistry at pages 486–500. The non-reactivity or inertness of the support in the latter case is shown by the fact that the support can be dissolved, e.g. in methanol, to give a crosslinked papain membrane. In these prior art techniques the enzyme crosslinking reagents have been bifunctional. These include: dialdehydes; monomeric polyisocyanates; bisamidoester; disulfonyl halides; and bisdiazobenzidine-2,2'-disulfonic acid.

Other techniques for immobilization of enzymes are disclosed in commonly assigned applications Ser. No. 615,156 filed 9/19/75 and U.S. Pat. No. 3,933,589.

Further details on such prior art techniques can be found in the book entitled "Biochemical Aspects of Reactions on Solid Supports", edited by George R. Stark, Academic Press, New York, N.Y. (1971); the article entitled "Enzymes Immobilized on Inorganic Carriers" by H. H. Weetall appearing in Research/Development, December (1971); the article entitled "The Potential Applications of Molecular Inclusion to Beer Processing" by R. A. Messing appearing in the December 1971 issue of the Brewer's Digest; U.S. Pat. No. 3,512,987 and 3,167,485.

While these prior art techniques are suitable for many applications, the need exists for a simple, efficient, and economical method for chemically immobilizing the enzyme urease to form an enzymatically active composite which retains a relatively high proportion of its initial activity even after conditions of prolonged storage and use.

Immobilized urease is particularly useful in the analysis of urea as set forth in U.S. Pat. No. 3,926,734.

It it recognized that the polymerization of urease has been studied in the past. For instance the articles "Urease Catalysis and Structure" VII. Factors Involved in Urease Polymerization and its Kinetic Pattern, by William N. Fishbein and K. Nagarajan, Archives of Biochemistry and Biophysics 144, 700–714 (1971); "Urease Catalysis and Structure" VIII. In this article a procedure is reported in which urease is purified by gel filtration chromatography. It seems clear, however, that no immobilization of urease takes place during this procedure. In all the chromagraphs illustrated in the article, the urease fractions are eluted in the void volume thus indicating no binding to the urease column. Furthermore, 85 to 95 percent of the urease can be accounted for by analysis of eluent fractions using the Folin Phenol test for amino acids. Thus, this article shows the chromatography of urease by gel filtration in which the urease peak containing soluble urease polymers is eluted in the void volume of the column (i.e. without binding to the column) and within experimental error all the protein including urease applied to the column is eluted. The articles include "Ionic Strength Dependence of Urease Polymerization and Polymer", by William N. Fishbein and K. Nagarajan, Archives of Biochemistry and Biophysics, 151, 370–377 (1972); "Spectrum of Urease: Genetic, Polymeric and Conformeric" by William N. Fishbein, Carlos L. Spears, and Warren Scurzi, Nature, Vol. 223, 191–193 (July 12, 1969); and "Urease Catalysis and Structure" IX. The Half-Unit and Hemipolymers of Jack Bean Urease, by William N. Fishbein, K. Nagarajan, and Warren Scurzi, The Journal of Biological Chemistry, Vol. 248, No. 22, 7870–7877 (1973) discuss parameters affecting the polymerization of urease but do not concern the immobilization of urease or the polymerization of urease on a support.

The present invention represents an advance over these techniques by providing for the polymerization of proteins and enzymes by in-situ reaction on an inert support to form a biologically active composite having prolonged service life.

In attaining the objects of this invention, one feature resides in the process for immobilizing a protein, preferably an enzyme on a support to form a biological active composite, comprising the steps of selecting a protein having the sum total of one-half of the cystine amino acid residues plus the cysteine amino acid residues equaling at least about 14 per mole of said protein, depositing said protein on an inert support to form a protein/support composite, and maintaining said composite at a pH which facilitates polymerization of said protein and maintaining said composite at a temperature and for a time sufficient to polymerize said protein and immobilize said protein in-situ on said support.

In the practice of the present invention the selection of the protein (e.g. the enzyme) having the sum total of one-half of the cystine amino acid residues plus the cysteine amino acid residues equaling at least about 14 per mole is important. While not being bound by any theory, it appears that the immobilization reaction involves a disulfide rearrangement within the protein molecule. Either the cystine or cysteine amino acid residues can be zero so long as the sum total of the two fulfills the ratio set forth above. However, when no cysteine is present, it may be necessary or desirable to add a trace of a compound containing sulfhydryl groups (e.g. an amount such that the reaction mixture is $10^{-8}$ to $10^{-5}$ molar in sulfhydryl groups) such as β-mercaptoethanol or dithiothrieitol, to initiate the disulfide interchange reaction. The term "amino acid residue" is used herein in its conventional sense and refers to the residues of the amino acids which chemically combine in forming the protein molecule.

It is known that the cysteine amino acid residues contain the —SH group and the cystine contains the —S—S— group, and under the pH condition specified herein these groups are theorized to undergo a disulfide rearrangement which results in the polymerization of the protein. This disulfide rearrangement is acid and base catalyzed and does not proceed at an acceptable rate at a pH in the range of about 6.6 to about 9.4. Whether or not this theory is responsible for the mechanism of the present invention is not significant because the advantages of invention have been experimentally established.

The proportion of cysteine and cystine represented by the number 14 as above has been discovered to be significant by experimentation in that those proteins and enzymes containing less than this proportion of cysteine and cystine amino acid residues do not appear to reliably polymerize according to the inventive principles.

The following table sets forth the cysteine and cystine proportions for several enzymes useful in the practice of the present invention.

| Enzyme | Molecular Weight | Cysteine amino acid residues (i.e. SH group) plus one-half cystine amino acid residues (i.e. one-half -S-S-) per mole |
|---|---|---|
| urease (Jack Bean) | 500,000 | 85 |
| histidase | 210,000 | 17 |
| L-amino acid oxidase | 135,000 | 14 |
| alcohol dehydrogenase (horse liver) | 40,000 | 28 |
| bovine serum albumin | 66,000 | 36 |
| albumin egg (slow) | 68,000 | 18 |
| albumin egg (fast) | 68,000 | 14 |

Other proteins in the form of enzymes which are particularly suited for the practice of the invention are urease, alcohol dehydrogenase, histadase, L-amino acid oxidase, $G_c$-globulin, glucose-6-phosphate dehydrogenase ED 1.1.1.49, glucose-6-phosphate dehydrogenase, glutamate synthase, glutamine phosphoribosylpyrophosphate amidotransferase P-300 monomer, glutaminyl-tRNA synthetase, glutathione synthetase, glyceraldehyde-3-phosphate dehydrogenase, glycerol-3-phosphate dehydrogenase, EC 1.1.1.8, glycine N-methyltransferase, glycinin, glycogen synthetase, glycoprotein, $a_2$-glycoprotein, histadine, $\beta_2$-glycoprotein, haptoglobin, hemocyanin, histidine ammonialyase and other enzymes as described in "A Compilation of Amino Acid Analyses of Proteins. VIII", Analytical Biochemistry, 66, 303–329 (1975) by Donald M. Kirschenbaum and other articles in this series by Kirschenbaum.

In practicing the present invention, an acid pH which facilitates polymerization is in the range of about 3 to about 6.5 and preferably in the range of about 4.5 to 6 for efficiency and economy. A basic pH which facilitates polymerization is in the range of about 9.5 to about 11.

For urease, the polymerization reaction apparently proceeds efficiently at the isoelectric point of urease which is at pH 5.1. Urease and other enzymes denature in strong acids and bases, and this factor must be considered in selecting the pH conditions for polymerization. It has been observed that sufficient polymerization of urease does not take place at pH 8.2 during the several hour period set forth herein to result in prolonged service life (see Example 4 of U.S. Pat. No. 3,926,734).

In carrying out the process of the present invention the enzyme or other protein and support are brought into contact in an aqueous solution of enzyme and the enzyme thoroughly wets and permeates the support. The pH of the enzyme solution is maintained as indicated above for time and temperature sufficient to polymerize the enzyme for immobilization in-situ on the support. This usually requires time periods ranging from a few minutes to several (e.g. 100) hours depending on the temperature, concentration, enzyme and other factors. Time periods of 1 to about 50 hours are suitable for most applications. The temperature is usually maintained below about 50° C to prevent denaturing the enzyme and temperatures in the range of about 0° C to 20° C are satisfactory for most applications.

In accomplishing this contact the enzyme or other protein is preferably first deposited (e.g. sorbed or impregnated) in or on the support. "Sorbed" is used to include adsorption or absorption by soaking the support with an aqueous solution of the enzyme. The aqueous solution is usually buffered to a pH of about 7.5 to 9 to prevent premature polymerization thereof. The amount of enzyme used per given weight or volume of support can be quite variable because of wide differences in porosity and surface activities of the supports as well as the variation in purity and composition of enzyme preparations which can be used in practicing this invention. The immobilized enzyme composite should contain at least about 0.001 Enzyme Units (U.) per cubic centimeter or ml for practical efficiency. The enzyme concentration in the reaction solution can be in the range of about 0.01% to about 90% by weight depending on solubility parameters.

An Enzyme Unit (U.) of biological activity has been defined as the amount of active enzyme which converts substrate to product at the rate of one micromole per minute.

The enzyme solution is adjusted to the pH which facilitates polymerization after contact with the support or shortly therebefore so long as premature polymerization does not prevent sorption on the support. This pH adjustment is accomplished by the addition of ordinary acids (e.g. HCl or $H_2SO_4$) or bases (e.g. NaOH, KOH) or buffers (e.g. acetate or phosphate buffers) as required. Quite often dilute buffer solutions which do not detrimentally affect the enzyme are employed, although strong acids and bases can be used under conditions which do not materially denature the enzyme. A few tests will establish whether or not a particular pH adjusting additive will detrimentally affect the enzyme.

It is an important feature of the present invention that the enzyme be deposited on the support prior to adjusting the pH to facilitate polymerization or shortly (e.g. a few minutes) thereafter. As an enzyme "monomer" it can efficiently penetrate and permeate the support to achieve the maximum amount of enzyme per unit of surface area, volume or weight of the enzyme/support composite. In some cases the enzyme can be first reacted with a mercaptan such as $\beta$-mercaptoethanol or cysteine to "depolymerize" any enzyme before contact with the support.

The immobilization techniques of the present invention are particularly useful in immobilizing urease for analysis of urea according to U.S. Pat. No. 3,926,734. The support is inert in this reaction sequence and the enzyme is not believed to be covalently bonded to the support.

The composition of the support is not particularly critical as long as it is inert, dimensionally stable, and provides sufficient surface area for retention of enzyme. The support can be porous, fluid-permeable membranes as in U.S. Pat. No. 3,839,175 or porous particulates as in U.S. Pat. No. 3,850,751. When porous supports are used, they should be sufficiently porous and sorptive enough to retain enough enzyme to form a biologically active composite. In the commercially significant embodiments of the present invention, the immobilized enzyme/support composite will exhibit at least about $1 \times 10^{-4}$ Enzyme Units (U.) of activity per cubic centimeter of composite. Low enzyme activities in the composite are often due to impure enzyme sources used in the preparation.

The technique of the present invention can also be used to polymerize urease when deposited in accordance with U.S. Pat. No. 3,839,175 or copending application Ser. No. 395,975 filed 9/10/73.

It has been found that the porous particles or the porous matrix having a volume porosity in the range of 10 percent to 80 percent and preferably in the range of 15–50 percent are quite suitable for the present purposes. The pore size of the support is critical in that it should not be so small as to prevent immobilization of the enzyme thereon. Average pore size diameters of either fluid permeable membrane or porous particulates in the range of 0.01 micron to 10 microns are suitable for most applications with 0.01 to 2 being preferred for efficiency and economy.

The porous particulate support can be refractory ceramic oxide powders such as alumina powder, zirconia powder, magnesia powder, silica powder, thoria powder, glass powder, powdered clay, powdered talc and the like. The particle size of the porous particulates is not critical although a size range of −5 mesh to plus 400 mesh is practical. For efficiency and economy the size fraction of −20 to +100 mesh (U.S. Sieve) is usually employed.

Porous, inert, rigid, dimensionally stable refractory fluid permeable membrane supports can be prepared by compacting such refractory oxide powders to form a "green compact" of the desired configuration. The green compacts are then fired for a time and at a temperature sufficient for sintering to yield porous, inert, rigid, dimensionally stable, fluid permeable refractory supports. The sintering should not be at a temperature or for a time which would cause collapsing or coalescence of the particles to form a non-porous body. A convenient indication of the degree of sintering is a comparison of the actual density of the fired compact as compared to the theoretical density of the oxide being fired. Of the many oxides which can be used for the present purposes, alumina is preferred for its chemical durability and ease of fabrication.

In forming the support from the powdered refractory oxide, the powdered particle size is selected to yield a sintered compact having a porosity and pore size in the range set forth above. The techniques for compaction and sintering of the porous supports are well-known in the art and form no part of the present invention. Suffice it to say that compacting pressures in the range of 1,000 psi to 10,000 psi and sintering temperatures in the range of 1,000° to 1,700° C are commercially expedient. Additional details on compacting and sintering of refractory oxides can be obtained from the book "Oxide Ceramics" by E. Ryshkewitch, published in 1960 by Academic Press, New York, N.Y.

The porous matrix can also be made of porous metal such as porous silver or porous stainless steel.

The porous matrix can be in any geometric shape such as rods, cylinders, discs, plates, bars, and blocks and the like.

Other suitable supports can be in the form of natural and synthetic fibers such as polypropylene, polyethylene, cotton or wool, nylon, rayon, polyester or acrylic fiber. The support can also be a blend of both natural and synthetic fibers or can be inorganic fibers made from carbon, asbestos, glass or similar fibrous ceramics, such as aluminum silicates. Fibrous forms of metals such as copper and stainless steel can also be used. Support fiber diameters can range from about 0.001 to about 0.25 inch. Such fibrous materials are quite useful in forming filter cartridges as in U.S. Pat. No. 3,828,934 for in-line filtration applications where filtration and treatment with immobilized enzymes are accomplished in one application.

For convenience in disclosure, all patent documents and publications mentioned herein are incorporated by reference.

In the Examples that follow, all parts are parts by weight, all percentages are weight percentages, and all temperatures are in ° C unless stated otherwise.

EXAMPLE 1

Part A

Twenty grams of particulate porous alumina are washed with four liters of distilled water by swirling in a flask and decanting the cloudy supernatant liquid. The particulate alumina has a particle size in the range of from −80 to +100 mesh (U.S. Sieve) and an average pore size diameter of about 0.1 to 0.2 microns with a volume porosity of about 10% to 20%. The alumina is then washed on a vacuum filter with one liter of distilled water. Finally, the alumina is deareated by adding 300 ml of a 2 × $10^{-3}$ molar; pH 8.5, tris (hydroxymethyl) aminomethane-maleic acid buffer (tris-maleate) to the alumina and evacuating the flask continuously with a water aspirator vacuum for about 1 hour. This buffer is discarded and 300 ml of fresh tris-maleate buffer are added.

Part B

An aqueous urease solution is prepared by dissolving 0.56 g of urease (Miles-Servac, Batch 11) in 120 ml of 2 × $10^{-3}$M tris-maleate buffer. This solution is centrifuged for 20 minutes at 10,000 gravity forces. The resulting supernatant liquid is decanted from the precipitate and the supernatant is added to the alumina in tris-maleate buffer of Part A. This mixture of urease and alumina in buffer is mixed for 35 minutes at 0° to 5° C.

The urease supernatant solution is decanted from this alumina and is transferred to the second, fresh, sample of alumina (like that of Part A except that the particle size is −60 +80 mesh) which had been pretreated as described above in Part A. The resulting mixture is mixed for about 30 minutes at 0° to 5° C.

Part C

The pH of the solution above the alumina is 8.2. The pH is then adjusted to pH 5.0 by the slow addition of a 0.02 M sodium acetate-acetic acid buffer solution having a pH of 4.5. The buffer is prepared by titrating 0.02 M sodium acetate against 0.02 M acetic acid to a pH of 4.5. A total volume of 98.2 ml of this buffer is required for this pH adjustment of the enzyme-alumina mixture.

After the addition of the acetate buffer is completed, the resulting mixture is shaken for one hour at 0 to 5° C. During this period the urease polymerizes in-situ and the resulting polyurease polymer becomes immobilized and entrapped in and on the alumina support to form a biologically active composite.

The resulting "poly" urease/alumina composite is filtered and washed with about 1.5 liter portions of 3.0 M sodium chloride, 5 × $10^{-3}$ M -ethylene-diamine/tetracetic acid (EDTA) and 2.0 × $10^{-3}$ M tris-maleate buffer (pH 7.0). The "poly" urease/alumina composite is analyzed to have an activity of 212 U./cc of composite and is effective in prolonged use as in the analytical process of Example 4 of U.S. Pat. No. 3,926,734.

When the procedures of this Example are repeated except that Part C is eliminated the urease is not adhered to the alumina and rapidly loses its effectiveness after only brief use in the analytical process as set forth in Example 4 of U.S. Pat. No. 3,926,734.

EXAMPLE 2

Part A

Two 20 g samples of particulate porous alumina, (−60 to +70 mesh) are washed with four liters of distilled water and then deareated with about 300 ml of 2 × $10^{-3}$ M tris-maleate buffer (pH 8.9) under a water aspirator vacuum for approximately 1 hour.

Part B

One gram of urease (Miles Servac Batch 11) is dissolved in 120 ml of tris-maleate buffer (pH 8.9). After standing for about 15 minutes at room temperature, the urease solution is concentrated by ultrafiltration in an ultrafiltration cell (Model B 15 Manicon concentrator, from Amicon Corporation) to a residual concentrate volume of about 9 ml. In this ultrafiltration process, the urease is substantially retained and low molecular weight impurities permeate through the cell.

This concentrated urease solution is then diluted to a volume of 120 ml with tris maleate buffer (pH 8.9). After refrigeration overnight at 0° to 5° C the urease solution is centrifuged at 2000 gravity forces for 20 minutes and the supernatant liquid is slurried with one of the alumina samples described above together with 100 ml of the trismaleate buffer. The concentration of urease is approximately 4.6 mg/ml. The urease/alumina mixture is mixed at a temperature of 0° to 5° C for 35 minutes. This procedure is believed to further purify the urease solution.

Part C

The supernatant solution above the alumina from Part B is decanted and mixed with the second, pretreated, alumina sample and mixed for 30 minutes at 0° to 5° C. The pH of the urease solution at this point is about 8.2 and is adjusted to pH 5.0 by the addition of 90 ml of 0.02 M sodium acetate-acetic acid buffer, pH 4.4. The acetate buffer contains 0.1% by weight NaOCl as a bactericide. This mixture is agitated for about 3 hours at a temperature of 0° to 5° C. During this period the urease polymerizes in-situ and the resulting polyurease becomes immobilized and entrapped in on the alumina support to form a biologically active composite.

The resulting polyurease/alumina composite is filtered on a vacuum filter and washed with two liters of a solution which is 1.0 molar in sodium chloride, 5 × $10^{-3}$ molar in the disodium salt of ethylenediamine tetraacetic acid ($Na_2$EDTA), and 2 × $10^{-3}$ molar in tris-maleate buffer, pH 7.0. A sample of the urease/alumina composite, analyzed before washing, exhibits an activity of 257 U./cc. The washed composite has an activity of 117 U./cc. The washed composite is tested as in Example 1 and similar results are obtained.

EXAMPLE 3

Particulate, porous, alumina (mesh −60 +70) is washed with 4 liter of distilled water. Next 20.5 gm of this alumina is washed under vacuum in a flask with 200 ml tris-maleate buffer, 2 × $10^{-3}$ M, pH 8.5 and mixed for about 30 minutes. (The same buffer is used throughout this example.) The buffer is discarded and the alumina is washed again with an additional 200 ml of the buffer.

One gram of urease (Miles Servac, Batch 11) is dissolved in 100 ml of the buffer and 1.5 ml of β-mercaptoethanol. The resulting solution is stirred at 0° to 5° C for 1 hour followed by centrifugation at 16,000 gravity force for 25 minutes.

The supernatant is concentrated and purified to a volume of 5 to 10 ml using a Millipore 142 mm Laboratory ultra-filtration cell (Cat. No. xx42 142 Sl) at a pressure of 50 to 100 psig. The filter used in this cell is designated PSTM (Millipore). One hundred ml of buffer is added to the concentrated urease solution and the concentration procedure is repeated to a final volume of 3 to 10 ml.

This urease solution is diluted to 120 ml with buffer and added to the alumina, buffer mixture. The total volume is approximately 300 ml. The mixture is agitated for 30 minutes at 0° to 5° C and the supernatant solution of urease is transferred to a second sample of alumina prepared in the same manner as the first sample. The resulting mixture of urease is agitated for 30 minutes at 0° to 5° C and is adjusted from pH 8.1 to pH 5.0 with the 0.02 M sodium acetate-acetic acid buffer at pH 3.8. The mixture is then agitated for about 3 to 4 more hours at 0° to 5° C. During this period the urease polymerizes in-situ and the resulting polyurease becomes immobilized and entrapped in and on the alumina support to form a biologically active composite. At the end of this period the pH of the supernatant solution is 5.2.

One half of the composite is removed and washed with 1 liter of $2 \times 10^{-3}$ M tris maleate buffer, pH 6.4 containing $5 \times 10^{-3}$ M EDTA. The initial activity of the composite is 392 U./cc and is about 58 U./cc after storage for 10 months in the tris maleate buffer used in the washing step. The other half of the composite is reacted an additional 16 hours at 0° to 5° C as described above and then washed as described above. The initial activity of this composite is 39 U./cc. This indicates that the activity may tend to decrease with further polymerization of the urease although the immobilized urease is suitable for many applications.

EXAMPLE 4

Five ml of $10^{-3}$ M HCl, 1M NaCl are injected into a liquid chromatography column packed with −40 +50 mesh alumina particles of the same type as used in Examples 1 through 3. The column is approximately one inch in diameter and 20 inches in height and the solvent is $10^{-3}$ M tris maleate EDTA buffer, pH 8.6.

One and one-half gm of urease (Miles Servac, Batch 11) is dissolved 12 ml of distilled water. To this urease solution are added 10 microliters of 0.1 M β-mercaptoethanol. After stirring for ½ hour, the solution is centrifuged at 10,000 gravity forces for 15 minutes. Five ml of the supernatant are injected into the above described column and chromatographically purified. The fractions from the main peak were saved and mixed together. The procedure, including the regeneration with HCl-NaCl solution, is repeated with an additional 5 ml of supernatant. The combined urease fractions are stored in the refrigerator overnight at 0° to 5° C.

Sixty gm of −50 +60 mesh $Al_2O_3$ particles of the type as used in Example 1 to 3 are washed with 5 liters of distilled water. Next, the alumina is placed under vacuum in an evacuated flask for 45 minutes while in contact with 500 ml tris maleate EDTA buffer $10^{-3}$ M, pH 8.8. Gentle agitation of the flask every 5–10 minutes is performed. The supernatant is discarded from the alumina and the alumina, 200 ml of tris maleate, $2.5 \times 10^{-3}$ M, buffer at pH 8.3 and 480 ml of pooled urease fractions are mixed together. This mixture is agitated for about 30 minutes and the pH is adjusted to 4.6 with 150 ml 0.02 M sodium acetate-acetic acid buffer (at pH 4.7) together with 7.1 ml, 1N HCl. The urease solution turns white in appearance after this treatment.

The resulting mixture is then agitated for 2 hours at 0° to 5° C and agitation of the remaining mixture at 0° to 5° C is continued. Three fourths of the alumina is removed and washed with about 1 liter $2 \times 10^{-3}$ M tris maleate buffer, pH 7.5 and stored in this buffer. The initial activity of this composite is analyzed to be 307 U./cc and 164 U./cc after 4 months of storage in the buffer.

The remaining alumina is reacted for an additional 20 hours at 0° to 5° C to further polymerize the urease and is then washed with about 1 liter of the tris maleate buffer and stored in this buffer. The initial activity of the resulting composite is 241 U./cc.

EXAMPLE 5

This example is the same as Example 4 except that the reaction mixture consisted of 200 ml of $2.5 \times 10^{-3}$ M, pH 8.6 tris maleate buffer plus 369 ml of the chromatographically purified urease. The pH after mixing is 8.8 and more than 200 ml of 0.2 M sodium acetate-acetic acid buffer, pH 3.0 is used to adjust the pH 5.0 and reacted at 0° to 5° C with agitation for 2 hours. During this period the urease polymerizes in-situ and the resulting polyurease becomes immobilized and entrapped in and on the alumina support to form a biologically active composite.

The resulting alumina/urease composite is washed with 430 ml of a buffer solution containing $1.5 \times 10^{-3}$ M tris maleate and $10^{-3}$ M EDTA at pH 7.5 and then washed with 2 liter of distilled water. The initial activity of this composite is analyzed to be 233 U./cc of alumina. After three months of storage at 0° to 5° C in the tris maleate buffer, the activity is 39 U./cc.

EXAMPLE 6

This example is the same as Example 4 with the following exceptions. The supernatant from centrifugation of the urease solution is filtered through a 0.2 micron filter before injection into the chromatographic column. Only 30 gm of alumina (−40 +50 mesh) is used and washed under vacuum with 400 ml of tris EDTA buffer pH 8.8 ($10^{-3}$ M).

After mixing of the urease with the alumina for ½ hour, one-third of the alumina and ⅓ of the supernatant solution at pH 8.8 are separated and mixed together for an additional 2 hours.

The remaining ⅔ of the alumina urease solution is titrated to pH 5.0 with dropwise addition of 20 ml of 0.1 M acetic acid and reacted at 0° to 5° C for 2 hours to polymerize the urease in-situ. Both alumina samples are washed with about 1 liter of $10^{-3}$ M tris EDTA, pH 7.5. Finally, both alumina samples are stored in the wash buffer solution at 0° to 5° C. The sample which had been reacted at pH 5.0 has an initial activity of 153 U./cc while the other sample which has been reacted at pH 8.8 has an initial activity of 96 U./cc. After storage for 8 days in this buffer the activity of the sample which had been reacted at pH 5 is at 151 U./cc while the other sample has an activity of 49 U./cc

EXAMPLE 7

This sample is prepared in the same way as in Example 5 at pH 5.0 except that 60 gm of alumina is used and the urease solution is treated with 15 microliters of a 0.2 M β-mercaptoethanol solution. The initial activity is 177 U./cc and after three days of storage the activity is 229 U./cc. After one month of storage the activity is 251 U./cc.

The polymerized urease composite is suitable for prolonged and repeated use in urea analysis as in U.S. Pat. No. 3,926,734 and as many as 965 BUN determinations have been made by this technique over a period of months without loss of effectiveness.

EXAMPLE 8

Two ten gram samples of porous alumina as described above (−80 +100 mesh) are each washed with 1 liter of deionized, distilled water and dried at 140° C overnight. A solution of horse liver alcohol dehydrogenase is prepared by dissolving 216 mg (400 U) in 50 ml of $10^{-3}$M phosphate buffer, pH 7.5. The enzyme is from Sigma Chemical Company and is lot number 55C-8220. Twenty-five ml of this enzyme solution are added to each ten gm sample of washed alumina. One sample is adjusted to pH 4.8 with 1N HCl while the other is maintained at pH 7.5 and both samples are shaken at about 5° C for 3 hours to permit any polymerization reaction to proceed. Finally, both alumina samples are washed with 1 liter of 0.1 M phosphate buffer, pH 7.5.

The alumina enzyme composites are then assayed for active alcohol dehydrogenase by measuring the conversion of NAD to $NADH_2$ (see Vallee, B. L. and Hoch, F., Proc. Natl. Acad. Sci, 41, 327 (1955). Aliquot samples are measured at 30 sec., 1 min., 2 min., 3 min. and 5 min. during the assay procedure. The alumina enzyme composite is removed from the aliquots before measurement of the absorbance at 340 nm by a $0.2\mu$ filter. The initial activity of the sample at pH 7.5 is 0.45 U/cc $Al_2O_3$ while that of the sample at pH 4.8 was 0.045 U/cc $Al_2O_3$. Twelve days later, the samples are washed with buffer (approximately 200 ml) and reassayed. The activity of the pH 7.5 sample is 0.027 U/ml $Al_2O_3$ while the pH 4.8 sample is 0.054 U/ml.

EXAMPLE 9

Two samples of alumina (10 gms each) of mesh size −80 +100 as described above are washed with 500 ml of distilled water. A solution of histidase from pseudomonas fluoresens is prepared by dissolving 0.3 gm in 100 ml of $2 \times 10^{-3}$ M phosphate buffer, pH 9.2. The enzyme is obtained from Worthington Biochemical Corporation, Code: H 1S-2FA and has an activity of 90 U/mg.

Fifty ml of the enzyme solution are added to each alumina sample. One solution-alumina mixture is adjusted to pH 5.0 using 1NHCl and the other sample is maintained at pH 9.2. Both samples are shaken for two hours at about 5° C to allow any polymerization reaction to proceed followed by washing with 1 liter of 0.1 M pyrophosphate buffer at pH 9.2. The samples are assayed by the procedure of Tabor and Mehler, Methods In Enzymology, Vol. II, (Colowick, S. P. and Kaplan, N. O. eds.), pg. 228, Academic Press, Inc., New York (1955). Removal of alumina during spectrophotometric measurement at 277 nm is accomplished as described in Example 8. The activity of the sample at pH 5 is 42 U/ml $Al_2O_3$ while the pH 9.2 sample is 10 U/ml $Al_2O_3$.

EXAMPLE 10

Two samples of alumina of 5 gm each (−80 +100 mesh) as described above are washed with 500 ml of distilled water and dried at 140° C overnight. Ten mg of L-amino acid oxidase are dissolved in 20 ml of $10^{-3}$ M TRIS-HCl buffer, pH 7.8. The activity of the enzyme is approximately 3 unit/mg as obtained from Worthington Biochemical Corporation (Lot LAO2CA).

Ten ml of the resulting enzyme solution are added to each alumina sample. One mixture is adjusted to pH 4.8 with 1N HCl and the other is maintained at pH 7.8. Both samples are allowed to shake at 5° C for 3 hours to allow any polymerization reaction to proceed. Next the enzyme alumina composites are washed with 500 ml of 0.2 M TRIS-HCl, pH 7.8. The assay is carried out as described by Curti, G., et.al., J. Biol. Chem., 243, 2306 (1968) using an oxygen electrode (YSI Model 53, Oxygen Monitor). The activity of the sample at pH 7.8 is 1.31 U/ml $Al_2O_3$ while that of the sample at pH 4.8 is 3.53 U/ml $Al_2O_3$.

EXAMPLE 11

One and a half grams of urease (Miles, batch 11) is dissolved in 50 ml of 0.5 M NaCl. To this solution 0.03 ml of 0.2 M β-mercaptoethanol is added. The solution is stirred for one-half hour to dissolve the urease. After one hour of stirring at room temperature, the resulting urease solution is centrifuged at 10,000 g for 30 minutes. While the above procedure is taking place, sixty gm of porous alumina like that of Example 1 (−40+50 mesh) is washed with 2 liters of distilled water.

The alumina is stirred in 500 ml of TRIS-EDTA $10^{-3}$ M buffer (pH 8.8) and vacuum operated for 1.5 hours. The buffer is discarded and the alumina is added to the urease solution and stirred for ½ hour. The resulting mixture is titrated to pH 10.0 with a few drops of 0.1 NaOH. The titrated mixture is shaken at room temperature for three hours to permit the polymerization reaction to proceed. The mixture is then titrated to pH 6.0 with 0.1 N HCl. The resulting alumina/immobilized urease composite is washed with 2 liters of 0.1 M NaCl containing $1 \times 10^{-3}$M EDTA, pH 6.0, and then with 500 ml of $1 \times 10^{-3}$ M TRIS-EDTA, pH 7.5.

The immobilized urease is then stored in $1 \times 10^{-3}$ M TRIS-EDTA, pH 7.5 and assayed. The result of the assay showed the presence of 950 U of urease activity per cc of alumina. After two days of use in urea analysis as in U.S. Pat. No. 3,926,734 no loss in activity is detected.

Having thus described the invention, what is claimed is:

1. In the process for immobilizing a protein on a support to form a biological active composite, the improvement comprising the steps of:
    selecting a protein having the sum total of one-half of the cystine amino acid residues plus the cysteine amino acid residues equaling at least about 14 per mole of said protein;
    depositing said protein on an inert support to form a protein/support composite; and
    maintaining said composite at a pH which facilitates polymerization of said protein and maintaining said composite at a temperature and for a time sufficient to polymerize said protein and immobilize said protein in-situ on said support.

2. The process of claim 1 wherein said protein is an enzyme.

3. The process of claim 2 wherein said pH is in the range of about 3.0 to about 6.5.

4. The process of claim 2 wherein said pH is in the range of about 9.5 to about 11.

5. The process of claim 2 wherein said inert support is a refractory oxide powder.

6. The process of claim 2 wherein said support is a porous matrix formed by compacting and sintering a refractory oxide powder.

7. The process of claim 2 wherein said support is in the form of fibers.

8. The process of claim 2 wherein said enzyme is deposited on said support by soaking said support in an aqueous solution of said enzyme.

9. The process of claim 2 wherein the enzyme is urease.

10. In the process for immobilizing urease on a support the improvement comprising the steps of:
contacting said support with an aqueous solution of a urease, maintaining the pH of said solution at a pH which facilitates polymerization of said urease, maintaining said urease at a temperature and for a time sufficient to polymerize said urease and immobilize said urease in-situ on said support.

11. The process of claim 10 wherein said support is porous aluminum oxide powder.

12. The product of the process of claim 1.

13. The product of the process of claim 2.

14. The process of claim 10 wherein the temperature of polymerization is less than about 50° C.

15. The process of claim 10 wherein the time required for polymerization is less than about 50 hours.

16. The process of claim 10 wherein said pH is in the range of about 4.5 to about 6.

17. The product of the process of claim 10.

18. The process of claim 10 where the temperature of polymerization is in the range of about 0° C to about 20° C.

* * * * *